United States Patent [19]

Feucht

[11] Patent Number: 4,745,918
[45] Date of Patent: May 24, 1988

[54] NEUTRAL ELECTRODE AND TERMINAL CLAMP THEREFOR

[76] Inventor: Peter Feucht, Feurigstr. 54, 1000 Berlin 62, Fed. Rep. of Germany

[21] Appl. No.: 929,570

[22] Filed: Nov. 10, 1986

[30] Foreign Application Priority Data

Dec. 16, 1985 [DE] Fed. Rep. of Germany ....... 3544483

[51] Int. Cl.⁴ ............................................ A61B 17/36
[52] U.S. Cl. ................................. 128/303.13; 128/798
[58] Field of Search ...................... 128/303.13, 303.14, 128/303.17, 908, 798, 802, 803, 640, 696; 339/255 P, 261, 174

[56] References Cited

U.S. PATENT DOCUMENTS

| | | | |
|---|---|---|---|
| 2,851,672 | 9/1958 | Odenwald | 339/255 P |
| 3,642,008 | 2/1972 | Bolduc | 128/798 |
| 3,721,246 | 3/1973 | Landis | 128/783 |
| 4,253,721 | 3/1981 | Kaufman | 339/91 R |
| 4,353,372 | 10/1982 | Ayer | 128/696 X |
| 4,384,582 | 5/1983 | Watt | 128/303.13 |
| 4,543,958 | 10/1985 | Cartmell | 128/640 |

FOREIGN PATENT DOCUMENTS

| | | |
|---|---|---|
| 2849422 | 11/1978 | Fed. Rep. of Germany . |
| 8205363.4 | 2/1982 | Fed. Rep. of Germany . |
| 2529075 | 6/1982 | France . |
| WO82/00414 | 2/1982 | PCT Int'l Appl. . |

*Primary Examiner*—Lee S. Cohen
*Attorney, Agent, or Firm*—Lawrence C. Edelman

[57] ABSTRACT

A split neutral electrode useful for electronic surgery, consists of at least a first and a second partial electrode separated from each other by an insulating strip. An electrical resistance establishes an electrical connection between the partial electrodes. Each partial electrode preferably has a protrusion which is wrapped around and makes forced contact with the resistance. An associated terminal clamp constructed in the form of an alligator clip contains two metal overlays which are brought into contact with the protrusions upon closure of the clamp.

16 Claims, 1 Drawing Sheet

NEUTRAL ELECTRODE AND TERMINAL CLAMP THEREFOR

BACKGROUND OF THE INVENTION

1. Field of the invention

The invention relates to a neutral electrode for high-frequency surgery which conducts a high-frequency surgical current from a patient and has at least first and second flat partial electrodes which are separated from each other by an insulating strip. The invention further relates to a terminal clamp for such a neutral electrode.

2. Description of the Prior Art

A split neutral electrode for high-frequency (HF) surgery (i.e., one which operates with two flat partial electrodes) has been described, for example, in German Utility Model (GM) Patent 82 05 363. As described therein, monitoring of the effectiveness of the electrical connection to the patient is accomplished by means of a control circuit using a low frequency control current. The control current flows from the contact surface of one partial electrode through the skin of the patient, to the contact surface of the other partial electrode.

German patent application publication DE-OS 28 49 422 describes another two part (i.e., split) neutral electrode.

Single neutral electrodes are also known in the present state of the art. HF-surgical apparatus is often equipped with a monitoring circuit with which it may be determined if the single electrode is in fact operational i.e., connected. For this purpose, first and second connecting leads are attached to the surface of the single part electrode. A control current is caused to flow from the first connecting lead through the neutral electrode to the second connecting lead. If the control current exceeds a pre-set threshold value, it may be safely assumed that the single electrode is in fact operational and has not lost sufficient electrical contact and/or fallen off. The embodiment of the neutral electrode proposed herein relates especially to this type of monitoring circuit.

It is now established that surgical procedures using a neutral electrode of the multiple partial electrode type are also desirable. A monitoring circuit is employed during the surgical procedure to determine whether the neutral electrode has large surface contact with the patient or just limited surface contacts. A monitoring circuit of this kind is described in a U.S. Patent Application by the same applicant and assignee herein, entitled "Method and Apparatus for Monitoring the Surface Contact of a Neutral Electrode of a HF-Surgical Apparatus", filed concurrently with the present application. It is desirable to form such a two or multiple partial neutral electrode in such a manner that it can be employed with a conventional monitoring circuit (i.e., one intended for use with a single neutral electrode) to make it possible to test whether the neutral electrode is in fact connected to the HF-surgical apparatus. This desire encounters the following difficulty: When one or more insulating strips are provided between the partial neutral electrodes, a direct current (or a low-frequency alternating current) applied to the neutral electrode cannot be used to check whether they are are present, since there can be no current flow between the partial electrodes due to the insulating strips.

SUMMARY OF THE INVENTION

The object of the present invention is to form a neutral electrode of the type including at least two partial electrodes in such a manner that it may be employed in combination with conventional monitoring apparatus for determining whether the neutral electrode is connected, in spite of the presence of one or more insulating strips between the partial electrodes. A further object of the present invention is to provide a terminal clamp for advantageously connecting this neutral electrode with the monitoring apparatus.

The first mentioned object is achieved, according to the invention, by arranging an electrical resistance between the two partial electrodes. The resistance is in contact with the two associated partial electrodes and when necessary, the resistance, and the partial electrodes are assembled into a single component.

The second mentioned object is achieved, according to the invention, through a terminal clamp for this neutral electrode that is exemplified by two conducting overlays in a housing body which can be brought into forced contact with the two partial electrodes by means of an operating element.

Other features and advantages of the invention will be apparent from the following description of the preferred embodiment, and from the claims.

For a fuller understanding of the present invention, reference should now be made to the detailed description of preferred embodiment of the invention and to the accompanying drawing.

DETAILED DESCRIPTION OF THE INVENTION

Figure 1:
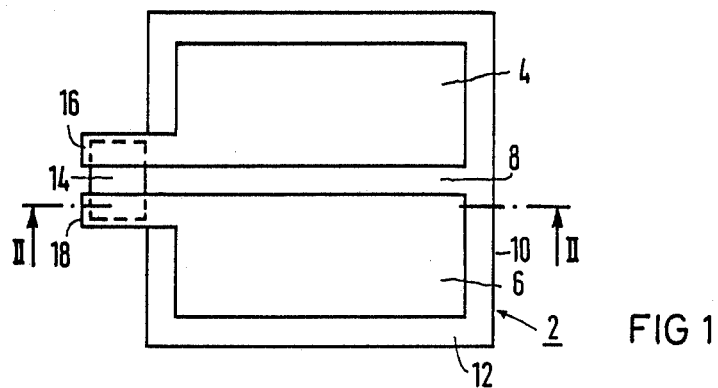
FIG. 1 illustrates a top view of a two-part neutral electrode including a monitoring resistance.
Figure 2:
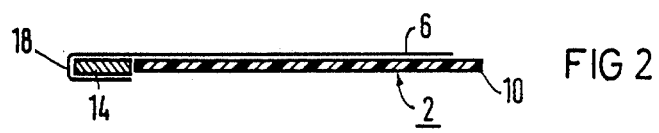
FIG. 2 illustrates a cross-section view of the neutral electrode of FIG. 1.

FIGS. 1 and 2 show a neutral electrode 2 useful in high-frequency (HF) surgery for conducting a high-frequency surgical current from the patient.

Neutral electrode 2 is split into first and second partial electrodes 4 and 6, respectively, each having a flat surface and being separated from each other by an insulating strip 8. Partial electrodes 4 and 6 each consist of a metal foil, or of a metal mesh, that is attached to a flexible backing 10. Backing 10, which is preferably designed to be self-adhesive, extends beyond the edge of partial electrodes 4 and 6. Electrodes 4 and 6, as well as backing 12, are essentially of rectangular shape.

An electrical resistance 14 is arranged between, and in electrical contact with, electrodes 4 and 6. Resistance 14 is of a relatively flat construction, and electrodes 4 and 6, resistance 14, and backing 10 are assembled into a single component. The construction is so selected that, to the extent possible, it results in a simple and economical configuration so that neutral electrode 2 could, if desired, be a low cost throw-away item.

In order to make resistance 14 an integral part of neutral electrode 2, each of partial electrodes 4, 6, is provided with a respective electrically conducting protrusion 16, 18 pointed in the same direction, i.e., to the left in the Figures. Protrusions 16 and 18 are formed from electrodes 4 and 6, respectively, are of lengthwise rectangular form and are forced into electrical contact with resistance 14. As shown in FIG. 2, protrusions 16 and 18 are bent into a "U"-shape, as seen from the side. Electrical resistance 14 is located in the space between wrapped around protrusions 16 and 18 and connected protrusions 16 and 18 together.

Electrical resistance 14 preferably consists of a piece of hard paper, the two opposing sides of which are coated with a conductive overlay. As shown in FIGS. 1 and 2, the hard paper is formed as a square. The overlay may be an evaporated layer of metal, for example, or applied as a layer of conductive paste. Advantageously, both sides of the hard paper may be overlayed with graphite, although, in principle, a single sided overlay is also possible.

It is again noted that projections 16 and 18 are narrow conducting strips, and that partial electrodes 4 and 6 are integrally formed with a respective one of protrusions 16 and 18. Protrusions 16 and 18 are arranged in the middle region of neutral electrode 2, i.e., they form an extension of insulating strip 8 between electrodes 4 and 6. The wrapped around portions of protrusions 16 and 18 are electrically joined to resistance 14 in a suitable manner, e.g., crimping and/or by soldering.

In the illustrated embodiments, the conductive surfaces of wrapped around protrusions 16 and 18 serve not only to fasten to resistance 14, but at the same time, as a counterpart for a terminal clamp 20. Clamp 20 is provided with two electrically connecting leads 22 and 24 and is shown in more detail in FIGS. 3 through 5.

During monitoring of neutral electrode 2 for connection, a control current is introduced into one of protrusions 16 or 18. In a conventional technique, a direct current may be employed. This flows, for example, from protrusion 16 through resistance 14, to protrusion 18. The current flowing from protrusion 18 is monitored by a control circuit (not shown). In the event that the current is zero, it is probable that neutral electrode 2 is not connected at all, or improperly connected to the HF-surgical apparatus. Thus, the control current may be used to check whether or not neutral electrode 2 is ready for use.

So far it has been assumed that a neutral electrode is split into two partial electrodes 4 and 6. In principle, the construction that has been described may also be applied to a neutral electrode split into three or more sub-divided electrodes. In that case, an individual electrical resistance would be arranged between and in electrical contact with each of two associated partial electrodes.

Figure 3:
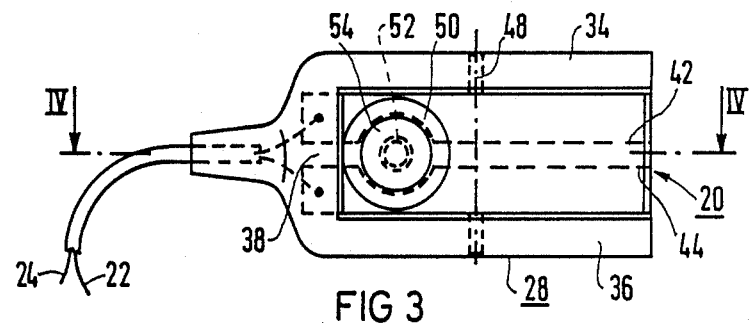
FIG. 3 illustrates a top of an electrical terminal clamp for the neutral electrode of FIG. 1.
Figure 5:
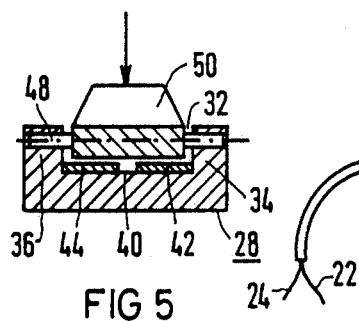
FIG. 5 illustrates a cross-section view of the terminal clamp of FIG. 4.
Figure 4:
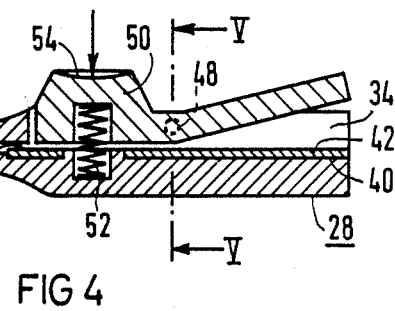
FIG. 4 illustrates a cross-section view of the terminal clamp of FIG. 3.

As shown in FIGS. 3 through 5, terminal clamp 20, which is similar in form to an alligator clip, comprises a housing body 28 preferably made of plastic. Housing body 28 is essentially of rectangular shape and has a formed cable feed-through with a channel 30 for accepting electrical connecting leads 22, 24.

Housing body 28 has a recess 32 having two opposite side walls 34 and 36, a rear wall 38 and a bottom 40. Recess 32 is "U"-shaped as shown in FIG. 5. Two extended overlays 42 and 44 of electrically conductive material, e.g., two metal strips, are located on bottom 40 of recess 32. Each of overlays 42 and 44 are electrically connected to a respective one of connecting leads 22 and 24.

An essential element of clamp 20 is a tipping axis 48 located at about mid-length along side walls 34 and 36. An operating element 50 is positioned to swivel about tipping axis 48. Operating element 50 is preferably made of plastic and is located substantially within recess 32. In addition, a spring element 52 is provided which exerts a force on operating element 50 which presses its forward part (the right end in FIG. 4) in the direction of conductive overlays 42 and 44.

The forward part of operating element 50 is essentially formed as a plate from tipping axis 48 onward, while its back part has a raised construction and is provided with a pressure pad 54 for the finger of an operator (user). When pressure is applied on pressure pad 54 (as shown by the arrow in FIGS. 4 and 5), terminal clamp 20 is caused to open.

More particularly, a coil spring is employed as spring element 52 (as shown by the arrow in FIGS. 4 and 5), which is supported at one end in a depression in the housing body 28 and at the other end in a depression in the back part of operating element 50. As shown in FIG. 4, the forward part of operating element 50 is inclined toward the rear part. In other words, the base of the foward part of operating element 50 facing bottom 40, is at an angle with respect to the base of the rear part. As is shown in FIG. 3, conductive overlays 42 and 44 each exhibit a constriction following the curvature of pressure pad 54 in a region surrounding spring. 52. In this manner, secure current conduction is achieved with comparatively large surface areas at protrusions 16 and 18, in spite of the compact construction.

When monitoring a neutral electrode 2 constructed in accordance with FIGS. 1 and 2, a terminal clamp 20 is opened and protrusions 16 and 18 are tightly clamped through the operation of spring 52. The control current then flows, e.g., from connecting lead 22, through overlay 42, protrusion 16, resistance 14, protrusion 18, overlay 44 and then to connecting lead 24.

Thus, there has been shown and described a novel neutral electrode and terminal clamp therefor which fulfills all the objects and advantages sought therefore. Many changes, modifications, variations and other uses and applications of the subject invention will, however, become apparent to those skilled in the art after considering this specification and the accompanying drawings which disclose only a preferred embodiment thereof. For example, neutral electrode 2 could be split to include more than two partial electrodes. Furthermore, terminal clamp 20 may be constructed to include more than two overlays and allow the monitoring of current through two or more resistances. All such changes, modifications, variations and other uses and applications which do not depart from the spirit and scope of the invention are deemed to be covered by the invention which is limited only by the claims which follow.

What is claimed is:

1. A neutral electrode useful during high-frequency surgery for conducting a high-frequency surgical current from a patient, comprising:
   an electrode split into at least first and second flat partial electrodes;
   an insulating strip separating said partial electrodes from one another; and
   an electrical resistance placed between said partial electrodes and in electrically conductive contact with each of said partial electrodes, wherein each said partial electrode has an electrically conducting protrusion making contact with said resistance, each protrusion, as viewed from the side, is bent into a "U"-shape, and at least a portion of said resistance is placed within the interior space of each of said "U"-shaped protrusions, thereby making forced contact with said protrusions.

2. A neutral electrode useful during high-frequency surgery for conducting a high-frequency surgical current from a patient, comprising:
   an electrode split into at least first and second flat partial electrodes;
   an insulating strip separating said partial electrodes from one another; and
   an electrical resistance placed between said partial electrodes and in electrically conductive contact with each of said partial electrodes, said resistance and said partial electrodes being formed into a single component and said resistance being composed of hard paper provided with a conductive layer on the outside thereof.

3. A neutral electrode according to claim 2 wherein:
   said hard paper is formed as a square, and said conductive layer is deposited by evaporation or applied as a paste thereon.

4. A neutral electrode useful during high-frequency surgery for conducting a high-frequency surgical current from a patient, comprising:
   an electrode split into at least first and second flat partial electrodes;
   an insulating strip separating said partial electrodes from one another; and
   an electrical resistance placed between said partial electrodes and in electrically conductive contact with each of said partial electrodes, wherein each of said partial electrodes has an electrically conducting protrusion making contact with said resistance, each of said partial electrodes comprises a metal foil, or a metal mesh, said partial electrodes being electrically separated from each other by said insulating strip and attached to a flexible base, said protrusions being narrow, electrically conductive strips which form an extension of said insulating strip between said partial electrodes.

5. A neutral electrode according to claim 4, wherein:
   each partial electrode is formed integrally with a respective one of said protrusions.

6. A neutral electrode according to claim 5, wherein:
   said protrusions are formed as an electrical contact for mating with a terminal clamp.

7. A combination including a neutral electrode useful during high-frequency surgery for conducting a high-frequency surgical current from a patient, said combination comprising:
   a neutral electrode split into at least first and second flat partial electrodes;
   an electrically insulating strip separating said partial electrodes one from another;
   an electrical resistance placed between said partial electrodes and in electrically conductive contact with a portion of each of said partial electrodes, said portions of partial electrodes and said resistance being formed into an electrical contact; and
   a terminal clamp including a housing having two electrically connecting leads, said clamp providing a releasably engageable electrical connection of said connecting leads to said electrical contact.

8. A combination according to claim 7, wherein:
   a moveable operating element is connected to said housing and said housing includes two conducting overlays connected to said leads and placed inside said housing, which overlays can be brought into forced contact with said partial electrodes by means of movement of said operating element.

9. A combination according to claim 8, wherein said terminal clamp comprises:
   (a) a recess in said housing which includes two oppositely positioned side walls and a bottom;
   (b) said conductive overlays each comprise a lengthwise formation of electrically conducting material applied to the bottom of said recess, each overlay being attached to a respective one of said connecting leads;
   (c) a tipping axis supported by said side walls of said recess, said operating element being pivotable about said tipping axis, whereby said operating element is essentially contained within said recess; and
   (d) a spring element which exerts a force on said operating element which presses a forward part of said operating element in the direction of said conducting overlays.

10. A combination according to claim 9, wherein:
    said recess is "U"-shaped when viewed in section.

11. A combination according to claim 9, wherein:
    a back part of said operating element is raised from said forward part and provided with a finger pressure pad.

12. A combination according to claim 11, wherein:
    said forward part of the operating element is inclined toward the back part.

13. A combination according to claim 9, wherein:
    said spring is a coil spring, supported at one end by a depression in said housing and at the other end by a depression in said operating element.

14. A combination according to claim 13, wherein:
    each of said conducting overlays exhibit a constriction in a region which is near said spring.

15. A combination according to claim 9, wherein:
    a channel is provided in said housing through which said connecting leads are brought out of said housing.

16. A combination according to claim 15, wherein:
    said housing and said operating element are each made of plastic.

* * * * *